United States Patent [19]

Suresh et al.

[11] Patent Number: 4,855,275

[45] Date of Patent: Aug. 8, 1989

[54] CATALYST PERFORMANCE IMPROVEMENT VIA SEPARATE BORON ADDITION

[75] Inventors: Dev D. Suresh, Hudson; Michael J. Seely, Chagrin Falls; James F. Brazdil, Mayfield Village; Robert K. Grasselli, Aurora, all of Ohio

[73] Assignee: The Standard Oil Company, Cleveland, Ohio

[21] Appl. No.: 157,428

[22] Filed: Feb. 18, 1988

[51] Int. Cl.[4] .......................... B01J 23/16; B01J 23/18
[52] U.S. Cl. .................................... 502/353; 502/205; 502/208; 502/212; 502/215; 502/216; 502/303; 502/304; 502/311; 502/325; 502/340; 502/344; 502/349; 502/354; 558/325
[58] Field of Search ............... 502/202, 204, 205, 206, 502/208, 353, 354, 212, 215, 216, 303, 304, 311, 325, 340, 344, 349; 558/325

[56] References Cited

U.S. PATENT DOCUMENTS

| | | | |
|---|---|---|---|
| 3,544,616 | 12/1970 | Grasselli et al. | 502/202 |
| 3,956,181 | 5/1976 | Grasselli et al. | 502/202 |
| 3,988,359 | 10/1976 | Saito et al. | 502/202 |
| 4,044,042 | 8/1977 | Angstadt | 502/202 |
| 4,083,804 | 4/1978 | Saito et al. | 502/205 |
| 4,110,250 | 8/1978 | Angstadt | 502/202 |
| 4,212,766 | 7/1980 | Brazdil et al. | 502/205 |
| 4,405,498 | 9/1983 | Ebner | 502/205 |
| 4,415,482 | 11/1983 | Ebner | 502/209 |
| 4,711,867 | 12/1987 | Hatano et al. | 558/324 |

Primary Examiner—Anthony McFarlane
Attorney, Agent, or Firm—Michael F. Esposito; David J. Untener; Larry W. Evans

[57] ABSTRACT

A process for improving the performance of an ammoxidation catalyst comprising contacting said catalyst with a boron containing or heat decomposable boron compound to deposit boron on the catalyst.

12 Claims, No Drawings

CATALYST PERFORMANCE IMPROVEMENT VIA SEPARATE BORON ADDITION

BACKGROUND OF THE INVENTION

The present invention is directed to a novel procedure to improve the performance of oxidation and ammoxidation catalyst and the resulting catalyst produced therefrom. In particular, the present invention is directed to a procedure to improve the performance of an ammoxidation catalyst in the production of acrylonitrile or methacrylonitrile by ammoxidation of propylene or isobutylene in fluid bed reactors. A well-known problem associated with fluid bed reactors is that a part of the catalyst is continually lost from the reactor by being entrained in the gaseous reactor effluent. For this reason, it is conventional to regenerate used or spent catalyst after an appropriate period of time. Applicants' invention is directed to a novel procedure which is applicable equally to (1) improving the initial performance of the ammoxidation catalyst or (2) regenerating the used or spent catalyst after the appropriate period of time.

U.S. Pat. No. 3,882,159 to Callahan et al discloses a method for regenerating used or spent molybdenum containing catalyst. Callahan et al. observed that molybdenumcontaining oxidation catalysts tend to lose molybdenum over time. Accordingly, Callahan et al. teach that when supported particles of molybdenum oxide are added to the molybdenum depleted catalyst in an operating reactor, some of the molybdenum on the particle is transferred back to the catalyst causing regeneration of the catalyst.

U.S. Pat. No. 4,052,332 to D'Amore et al. discloses another technique for regenerating a used or spent bismuth molybdate ammoxidation catalyst whose molbdenum content has been depleted through extensive use. In accordance with the D'Amore et al. technique, the catalyst is withdrawn from the reactor and impregnated with a solution of bismuth and molybdenum in an amount sufficient to make up preferably at least 90% of the molybdenum lost from the catalyst. Since bismuth is not lost, the added bismuth increases the original content of the regenerated catalyst.

Finally, U.S. Pat. No. 4,311,611 to Sasaki et al. discloses a regeneration process for antimony containing catalyst comprising treating the deteriorated or spent catalyst with hydrogen peroxide.

While each of these techniques described above is capable of regenerating spent ammoxidation catalysts, each has its own disadvantages. For example, the D'Amore et al. technique requires the catalyst to be withdrawn from the reactor. This means that either the reactor has to be shut down, or only a portion of the catalyst may be withdrawn at any one time. In either event, the ammoxidation procedure obviously loses efficiency. The Callahan technique, while allowing for the in situ regeneration of the catalyst, provides limited improvement in the spent catalyst. All of the previously discussed techniques have the additional disadvantage that they are directed to only one type of catalyst. Applicant's invention provides a significant advance in the procedures described above because it can be utilized with more than one type of catalyst. That is, applicants' procedure can be utilized in improving or regenerating various types of catalyst, including molybdate based catalysts and antimonate based catalysts. Accordingly, applicants' procedure has an adaptability or flexibility not found in the previously described processes.

SUMMARY OF THE INVENTION

It is the primary object of the present invention to provide a novel procedure for regenerating used or spent ammoxidation catalysts.

It is another object of the present invention to provide a novel procedure for improving the performance of an ammoxidation catalyst.

It is a further object of the present invention to provide a novel ammoxidation catalyst.

It is a still further object of the present invention to provide an improved fluid bed process for the ammoxidation of propylene to acrylonitrile.

Additional objects, advantages and novel features of the invention will be set forth in part in the description which follows, and in part, will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the purpose of the present invention, as embodied and fully described herein, the method of the present invention comprises contacting an ammoxidation catalyst with a heat decomposable boron containing compound at an elevated temperature for a time sufficient to decompose the compound and deposit boron on the catalyst.

In a further aspect of the present invention, a process is provided for the ammoxidation of an olefin to its corresponding nitrile comprising contacting the olefin in the vapor phase with ammonia, oxygen and water in the presence of a catalyst wherein the improvement comprises contacting the ammoxidation catalyst with a heat decomposable boron containing compound under conditions that are substantially the same as the conditions for ammoxidation.

In a still further aspect of the present invention, a process is provided for the production of a catalyst having improved performance for the ammoxidation of an olefin to its corresponding nitrile comprising applying a boron containing compound to the surface of the catalyst.

The present invention represents a material improvement over the previously discussed procedures for regenerating or improving the characteristics of ammoxidation catalyst. As stated previously, the process may be used to obtain improvements in several types of ammoxidation catalysts. In addition, the process is particularly effective for use with molybdenum based catalysts and antimony based catalysts. Most especially, the process is effective for use with molybdenum-bismuth based catalysts and antimony-iron based catalysts. Typical examples of the types of catalysts which may be used in the practice of this invention are those set forth in U.S. Pat. Nos. 4,311,611, 4,316,855, and 3,882,159 herein incorporated by reference.

Reference will now be made in detail to the present preferred embodiments of the invention.

DETAILED DESCRIPTION OF THE INVENTION

In general, the process of the present invention is directed to the fabrication of a catalyst possessing improved performance during the ammoxidation of an olefin to its corresponding nitrile. In particular, the process of the present invention is directed to the fabrication of an improved fluid bed ammoxidation catalyst useful in the ammoxidation of propylene or isobutylene to acrylonitrile and methacrylonitrile.

Generally, ammoxidation reactions are characterized by the reaction of an unsaturated hydrocarbon in the vapor phase with ammonia, oxygen and a catalyst. When producing acrylonitrile the unsaturated hydrocarbon is propylene and when producing methacrylonitrile the unsaturated hydrocarbon is isobutylene.

The reactions are well known as evidenced by U.S. Pat. Nos. 3,882,159 and 4,311,611 herein incorporated by reference.

The invention is also applicable to any other type of oxidation reaction in which an organic reactant is catalytically reacted with molecular oxygen by means of a redox catalyst. Examples of such reactions are the oxidation of olefins such as propylene and isobutylene to produce the corresponding aldehydes and acids, and the oxydehydration of olefins such as isoamylenes to produce the corresponding diolefins.

Various oxide complex redox catalysts can be used to catalyze the above oxidation type reactions. In general, the process of the present invention may be used with several types of oxidation or ammoxidation reaction catalyst. However, the invention has particular utility in improving the performance of molybdate based catalyst or antimonate based catalyst. In particular, the bismuth molybdate catalysts of U.S. Pat. No. 3,642,930 and the iron antimony catalysts of U.S. Pat. No. 4,311,611 are ideally suitable for the practice of this invention.

The process of the present invention comprises contacting an ammoxidation catalyst with a heat decomposable boron containing compound at an elevated temperature for a time sufficient to decompose the compound and deposit boron on the catalyst.

The catalyst selected may be either fresh (unused) or spent (used). In addition, the base catalyst may or may not contain boron. Bismuth molybdate and iron antimonate catalysts are preferred.

Typically, the bismuth-molybdate based catalysts are characterized by the following formula:

$$Bi_aFe_bMo_cQ_dR_eT_fM_gO_x$$

wherein
Q is at least one element selected from alkali metals, Tl, In, Cu, Ag;
R is at least one element selected from W, Cr, Ce, Zn, Ge, Mn, Pb, Ba, Te, Sn;
T is at least one element selected from phosphorus, arsenic, antimony, boron;
M is at least one element selected from cobalt, magnesium and nickel;
wherein
a, b and c are numbers in the range of 0.1 to 12;
d is between 0.01 to 8;
e is between 0 to 8;
f is between 0 to 6;
g is between 0 to 12;
x is a number determined by the valency requirements of the other elements present.

The iron-antimony based catalyst may be characterized by the formula:

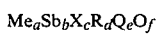

$$Me_aSb_bX_cR_dQ_eO_f$$

wherein
Me is at least one element selected from Fe, Co, Te, Ni, Mn, U, Ce, Sn and Cu;
X is at least one element selected from V, Mo, W, Nb, and Ta; R is at least one element selected from B, P, Bi and Te;
Q is at least one element selected from Mg, Ca, Sr, Ba, La, Ti, Zr, Cr, Re, Ru, Os, Rh, Ir, Pd, Pt, Ag, Cd, Al, Ga, In, Tl, Si, B, Ge, Pb, As, S, and Se; and
a=10;
b=5 to 60;
c=0 to 30;
d=0 to 10;
e=0 to 20;
f=number of oxygen atoms needed to satisfy the valency requirements of the formula;

It should be understood that the bismuth-molybdenum and iron antimony based catalyst described above are merely illustrative of the types of catalyst suitable for the practice of the present invention and other similar types of catalysts may be utilized in the practice of the present invention.

Typically, the elevated temperature is between the range of 200° C. and 600° C., most preferably between 400° C. and 500° C.

The contact time between the heat decomposable boron compound and the catalyst must be sufficient to allow for the decomposition of the heat decomposable boron compound and the deposit of the boron on the catalyst. In general, a contact time of between about 1 minute to 2 hours is sufficient.

In a preferred embodiment of the present invention, the heat decomposable boron compound is placed in solution prior to contact with the catalyst. Typical heat decomposable boron compounds are boron halides, boric anhydride, and boric acid. In addition, organoboron compounds such as boric acid esters may be utilized in the practice of the invention. Moreover, water or organic solvents such as methanol and ethanol may be utilized in the practice of the invention. While the exact amount of boron or boron containing compound added to the surface of the catalyst is not critical, typically catalyst having about 1 to 5 weight % H₃BO₃ have been utilized in the present invention.

In a further preferred embodiment of the present invention, the solution of heat decomposable boron compounds includes other regenerative components such as molybdenum oxide, bismuth oxide, tellurium oxide and antimony oxide.

In another preferred embodiment of the present invention, the process for fabricating a catalyst having improved performance during ammoxidation of an olefin to a corresponding nitrile comprises applying a boron containing compound to the catalyst. For example, boron containing materials such as boron oxide may be applied directly to the surface of the catalyst.

The conditions for applying the boron containing compound (i.e., boron oxide) directly to the catalyst surface are similar to those described previously. That is, the boron oxide may be applied by precipitation from an aqueous solution.

In a further aspect of the present invention, an ammoxidation reaction is disclosed wherein an olefin is converted to its corresponding nitrile in the presence of oxygen, olefin, and ammonia and an ammoxidation catalyst, wherein the improvement comprises contacting the ammoxidation catalyst under conditions that are substantially the same as the conditions of the ammoxidation reaction with a heat decomposable boron compound for a time sufficient to decompose the heat decomposable boron compound and deposit boron on the catalyst. Preferably, the boron compound is added continuously to the catalyst during the course of the ammoxidation reaction.

The conditions for the ammoxidation procedure are conventional and well known in the art and form no part of this invention. Typically, the ammoxidation conditions set forth in U.S. Pat. Nos. 3,882,159, 4,311,611 and 4,052,332 herein incorporated by reference may be utilized in the practice of this invention.

The exact mechanism by which one achieves the improved results of the present invention is not known. That is, it is not known if the boron remains on the surface of the catalyst or impregnates itself within the catalyst material. In addition, it is not known whether the boron remains in an elemental state or reacts with the catalyst to form boron compounds. However, it is clear that it is separate addition of boron to the already prepared catalyst which results in the improved catalytic performance observed during the practice of the invention.

To further illustrate the method of the present invention, the following examples are presented.

COMPARATIVE EXAMPLES A AND B

Example A

A molybdate based catalyst was used in a convention ammoxidation reactor under the following conditions: Temperature=445° C., contact time=2 seconds and Feed=1.8 propylene/2.2 NH$_3$ 3.6 O$_2$/2.4 N$_2$/6.0 H$_2$O. The resulting percent conversion and selectivity to acrylonitrile was 79.0% and 79.4%, respectively. The total C$_3$=conversion was 99.6%.

Example B

The same molybdate base catalyst used in Example A was treated with solid MoO$_3$. The resulting catalyst had additional 2 weight % MoO$_3$. Ammoxidation was performed under the same conditions as set forth in Example A. The resulting conversion and selectivity to acrylonitrile was 81.6% and 83.6%, respectively. The total C$_3$=conversion was 97.5%.

EXAMPLE 1

As illustrative of the improved results of the present invention, the same molybdate based catalyst used in Examples A and B was treated by the process of the present invention. That is, the molybate base catalyst was treated with MoO$_3$ and H$_3$BO$_3$. The resulting molybdate catalyst contained additional 2 weight % MoO$_3$ and 1 weight % H$_3$BO$_3$. Ammoxidation was then performed under the same conditions as set forth in Example A. The resulting conversion and selectivity to acrylonitrile was measured as 82.0% and 85.1%, respectively, with a total C$_3$=conversion of 96.4%.

The results of comparative Examples A and B and Example 1 are set forth below in Table I. The improved results of the present invention are readily apparent.

TABLE I

| Example | Catalyst Run | Temp. C. | Time | % C = Conversion to: AN | SEL | C$_3$= |
|---|---|---|---|---|---|---|
| A | Bismuth-molybdate base ammoxidation catalyst* | 445 | 2 sec | 79.0 | 79.4 | 99.6 |
| B | Bismuth-molybdate base ammoxidation catalyst* | 445 | 2 sec | 81.6 | 83.6 | 97.5 |
| 1 | Bismuth-molybdate base ammoxidation catalyst* | 445 | 2 sec | 82.0 | 85.1 | 96.4 |

Feed: 1.8C$_3$=/2.2NH$_3$/3.6O$_2$/2.4N$_2$/6.0H$_2$O

*Same catalyst used in Examples A, B and 1, catalyst did not contain B or antimony.

The following examples are set forth to illustrate the applicability of applicants' claimed process for antimony or antimony base catalysts containing boron.

COMPARATIVE EXAMPLE C

Example C

A fresh ammoxidation catalyst having the following formula 60% Cu$_{3.8}$ Cr$_2$ Te$_{1.7}$ W$_{.2}$ Mo$_{.5}$ Cs$_{.05}$ B$_{.5}$ Sb$_{18}$ Sn$_{30}$ O$_x$+40% SiO$_2$ was used in the ammoxidation of propylene to acrylonitrile. The conditions during ammoxidation were: Temperature 430° C., contact time 3.0 seconds and feed 1 propylene/1.2 NH$_3$/10.5 air/4 H$_2$O. The results were 47.5% conversion to acrylonitrile, 50.2% selectivity, total C$_3$=conversion of 94.6%.

Example 2

The same ammoxidation catalyst disclosed in Example C was treated with solid H$_3$BO$_3$ to produce a catalyst containing 2 weight % H$_3$BO$_3$. The resulting catalyst was used in an ammoxidation reaction under the same conditions as set forth in Example C. The results were: 71.8% conversion to acrylonitrile, 80% selectivity and total C$_3$=conversion of 89.7%.

Example 3

The ammoxidation catalyst of Example C treated in accordance with the procedure of Example 2 was used in an ammoxidation reaction at 445°. The results were: 73% conversion to acrylonitrile, 77.7% selectivity and total C$_3$=conversion of 93.9%.

Example 4

The following example illustrates the embodiment of the invention wherein the boron compound is placed in a solvent prior to contacting the catalyst.

An aqueous solution containing 1 weight % H$_3$BO$_3$ was prepared by conventional techniques.

The ammoxidation catalyst of Example C was treated with the aqueous solution containing 1 weight % H$_3$BO$_3$. The ammoxidation reaction was performed under the same condition as Example 3. The results were 76.8% acrylonitrile conversion, 82.4% selectivity and 93.2% total C$_3$=.

The results set forth in the above examples clearly demonstrate the improved performance of ammoxidation catalyst treated in accordance with the procedure set forth in the present invention.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended thereto.

What is claimed is:

1. A process for improving the performance of a calcined metal-antimonate based ammoxidation catalyst characterized by the formula:

$$Me_aSb_bX_cR_dQ_eO_f$$

wherein
Me is at least one element selected from Fe, Co, Ta, Ni, Mn, U, Ce, Sn and Cu;
X is at least one element selected from V, Mo, W, Nb and Ta;
R is at least one element selected from B, P, Bi and Te;
Q is at least one element selected from Mg, Ca, Sr, Ba, La, Ti, Zr, Cr, Re, Ru, Os, Rh, Ir, Pd, Pt, Ag, Cd, Al, Fa, In. Tl, Si, B, Ge, Pb, As, S, and Se;
a=10;
b=5 to 60;
c=0 to 30;
d=0 to 10;
e=0 to 20;
f=number of oxygen atoms needed to satisfy the valency requirements of the formula comprising contacting said calcined metal-antimonate based catalyst with a heat decomposable boron containing compound at a sufficient
elevated temperature and for a time sufficient to decompose the compound and deposit boron on the surface of said
calcined catalyst.

2. A process of claim 1 wherein said temperature is between about 400° C. to 500° C.

3. The process of claim 1 further comprising placing said heat decomposable boron compound in a solvent prior to contacting said catalyst.

4. The process of claim 3 wherein said solvent is water.

5. The process of claim 3 wherein said solvent is an alcohol.

6. The process of claim 1 wherein said catalyst is spent.

7. A process for improving the performance of a calcined ammoxidation catalyst comprising contacting said ammoxidation catalyst with a heat decomposable boron-containing compound during the ammoxidation of an olefin to its corresponding nitrile for a time sufficient to decompose said compound and deposit boron on the surface of said catalyst.

8. The process of claim 7 wherein said olefin is selected from the group consisting polypropylene and isobutylene.

9. The process of claim 8 wherein said nitrile is selected from the group consisting of acrylonitrile or methacrylonitrile.

10. The process of claim 7 wherein said catalyst is spent.

11. A process for improving the performance of a calcined metal-antimonate based ammoxidation catalyst characterized by the formula:

$$Me_aSb_bX_cR_dQ_eO_f$$

wherein
Me is at least one element selected from Fe, Co, Ta, Ni, Mn, U, Ce, Sn and Cu;
X is at least one element selected from V, Mo, W, Nb and Ta;
R is at least one element selected from B, P, Bi and Te;
Q is at least one element selected from Mg, Ca, Sr, Ba, La, Ti, Zr, Cr, Re, Ru, Os, Rh, Ir, Pd, Pt, Ag, Cd, Al, Fa, In. Tl, Si, B, Ge, Pb, As, S, and Se;
a=10;
b=5 to 60;
c=0 to 30;
d=0 to 10;
e=0 to 20;
f=number of oxygen atoms needed to satisfy the valency requirements of the formula comprising applying a boron-containing material to the surface of said calcined catalyst.

12. The process of claim 11 wherein said boron containing material is boron oxide.

* * * * *